United States Patent [19]

van der Burg

[11] 4,158,059
[45] Jun. 12, 1979

[54] TENSION REDUCING 2,3,4,4A,9,136-HEXAHYDRO-DIBENZ[1,2;5,6-]CYCLOHEPTA[3,4-C]PYRIDINES

[75] Inventor: Willem J. van der Burg, Heesch, Netherlands

[73] Assignee: Akzona Incorporated, Asheville, N.C.

[21] Appl. No.: 918,219

[22] Filed: Jun. 23, 1978

Related U.S. Application Data

[62] Division of Ser. No. 798,222, May 18, 1977.

[30] Foreign Application Priority Data

May 24, 1976 [NL] Netherlands .......................... 7605526

[51] Int. Cl.$^2$ .................... A61K 31/445; C07D 221/18
[52] U.S. Cl. ........................................ 424/267; 546/77; 546/78
[58] Field of Search .................... 260/293.54; 424/267; 546/77, 78

[56] References Cited

U.S. PATENT DOCUMENTS

| | | | |
|---|---|---|---|
| 3,636,045 | 1/1972 | Blattner et al. | 260/326.5 B |
| 4,002,632 | 1/1977 | van der Burg | 260/294.8 A |

OTHER PUBLICATIONS

Smrz, R. et al., *Coll. Czech. Chem. Commun.*, 1976, 41(11), 3420-3436 [Chemical Abstracts, 86:189679t (1977)].

*Primary Examiner*—John M. Ford
*Assistant Examiner*—Richard A. Schwartz
*Attorney, Agent, or Firm*—Robert H. Falk; Charles A. Wendel; Francis W. Young

[57] ABSTRACT

The invention relates to novel dibenzo[1,2;5,6] cyclohepta pyridine or -pyrrole derivatives, dibenzo[2,3;6,7] oxepino pyridine or pyrrole derivatives, dibenzo[2,3;6,7] thiepino pyridine or pyrrole derivatives and dibenzo[b,f] pyrido or pyrrolo azepine derivatives of general formula:

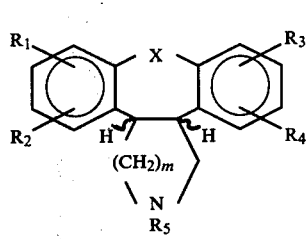

as well as the pharmaceutically acceptable salts and nitrogen oxides thereof, wherein $R_1$, $R_2$, $R_3$ and $R_4$ each represent hydrogen, hydroxy, halogen, an alkyl (1-6 C) group, an alkoxy or alkylthio group in which the alkyl group contains 1-6 C-atoms, or a trifluoromethyl group, $R_5$ represents hydrogen, an alkyl group with 1-6 carbon atoms or an aralkyl group with 7-10 carbon atoms, m is the number 1 or 2, X represents oxygen, sulphur, the group

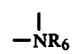

or the group —$CH_2$— and $R_6$ represents hydrogen or a lower alkyl group (1-4 C), having CNS-depressant activity and excellent antihistamine and antiserotonin activities.

36 Claims, No Drawings

TENSION REDUCING 2,3,4,4A,9,13B-HEXAHYDRO-DIBENZ[1,2;5,6]CYCLOHEPTA[3,4-C]PYRIDINES

This is a division, of application Ser. No. 798,222, filed May 18, 1977.

The present invention relates to novel biologically active tetracyclic compounds. More specifically, it relates to dibenzo[1,2;5,6]cyclohepta pyridine or -pyrrole derivatives, dibenzo[2,3;6,7]oxepino pyridine or pyrrole derivatives, dibenzo[2,3;6,7]thiepino pyridine or pyrrole derivatives and dibenzo[b,f]pyrido or pyrrolo azepine derivatives, to methods for their preparation and compositions containing them.

It has been found that tetracyclic compounds of general formula:

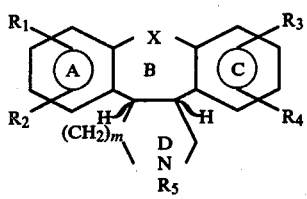

as well, as the pharmaceutically acceptable salts and nitrogen oxides thereof, wherein $R_1$, $R_2$, $R_3$ and $R_4$ each represent hydrogen, hydroxy, halogen, an alkyl (1-6 C) group, an alkoxy or alkylthio group in which the alkyl group contains 1-6 C-atoms, or a trifluoromethyl group, $R_5$ represents hydrogen, an alkyl group with 1-6 carbon atoms or an aralkyl group with 7-10 carbon atoms, m is the number 1 or 2, x represents oxygen, sulphur, the group

or the group —CH$_2$—and $R_6$ represents hydrogen or a lower alkyl group (1-4 C), show surprisingly valuable biological activities.

The compounds herein referred to show, in general marked CNS-depressant activity, which can be used in the treatment of states of tension, excitation and anxiety, and in the treatment of psychotic and schizophrenic conditions. Furthermore the compounds according to the invention show excellent antihistamine and antiserotonin activities.

Certain tetracyclic compounds, which are related to the compounds according to the invention, have been described already in the patent literature. Some compounds of formula I, in which the junction between ring B and ring D is unsaturated and wherein m has the value 1 have been discussed in U.S. Pat. No. 3,636,045, showing a similar biological pattern as found for the compounds according to the invention. In general, the present compounds, however, are surprisingly more active and, moreover, show in some cases a tendency of dissociation towards the neuroleptic activity.

Compounds of formula I, in which the ring junction between ring B and ring D is unsaturated and wherein m has the value 2 have been described in U.S. Pat. No. 4,002,632. These known compounds, however, show the opposite effect, namely a CNS stimulating activity, which, in general, can be used for the treatment of depressive conditions.

The compounds according to the invention may be prepared in a way which is usual for analogous compounds.

A very readily performed synthesis consists of the reduction of a compound of the general formula II:

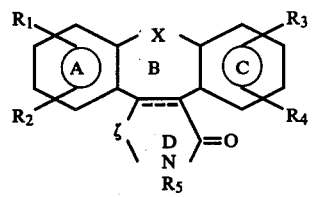

in which the dotted line represents an optional bond, Q represents a methylene, ethylene or vinylene group, and X, $R_1$, $R_2$, $R_3$, $R_4$ and $R_5$ possess the meanings given above.

Such a reduction is carried out in the way usual for the reduction of an amide group. Suitable reducing agents in this process are in particular the complex-metal hydrides, such as di-isobutyl-aluminum hydride, lithium borohydride, sodium trimethoxyborohydride, and especially lithium aluminum hydride.

If in addition to the keto group, one or more double bonds in a compound according to formula II are also to be reduced, it is recommendable that these double bonds are reduced first, since with the reduction method noted above these double bonds, and particularly the optional double bond between the B and the D rings, are only partially reduced. Suitable methods for first reducing these double bonds are: catalytic hydrogenation, e.g. PtO$_2$/H$_2$, treatment with magnesium in an alcohol, preferably methanol, or a Birch reduction (alkali metal in liquid ammonia, preferably sodium in liquid ammonia).

For a reduction by means of which both the keto group and the optionally present double bond(s) are simultaneously reduced in practically quantitative yield, use is preferably made of diborane, an alkali metal, e.g. sodium, in alcohol, or a mixture of lithium aluminum hydride and aluminum halide, e.g. AlCl$_3$.

The compounds according to the general formula II, required as starting materials, are prepared in one of the usual ways for this type of compound. One of these methods of preparation is shown schematically in the flow sheet hereinbelow.

Another method for the preparation of compounds I in which m=1 or 2 consists of the reduction of the double bond in a compound of general formula:

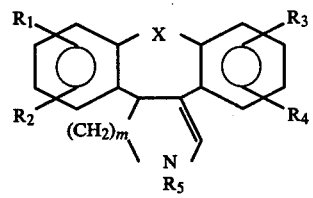

or a salt thereof, in which $R_1$, $R_2$, $R_3$, $R_4$, $R_5$ and X have meanings assigned above.

This reaction is carried out in a fashion usual for the reduction of an enamine, for example by means of complex metal hydrides such as sodium borohydride, lithium borohydride, by means of catalytic hydrogenation, for example $PtO_2/H_2$ or $Pd/C/H_2$, with an alkali metal in liquid ammonia (Birch reduction) or with the aid of formic acid.

The starting materials III may be isolated from the reaction mixture obtained from the reduction describes above of a compound of formula II (without any double bond in the D-ring), with the aid of $LiAlH_4$ or diborane (see flow sheet hereinbelow).

The latter method—the reduction of the enamine of formula III—is preferably utilized for the preparation of compounds I, in which m has the value 1. On reduction of a compound II (having no double bonds in ring D), in which m=2, with $LiAlH_4$ or diborane only a very small proportion is converted into a compound of formula III, while the same reduction applied to a compound II in which m=1 provides 25 to 50% of the enamine III concerned.

A further method for the preparation of the compounds of formula I, in which m=2, consists of the reduction of a compound of the general formula IV or IVA:

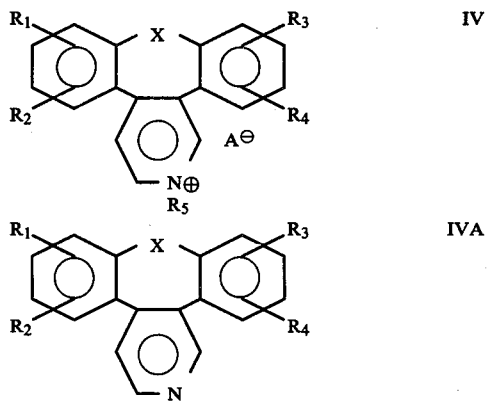

in which $R_1$, $R_2$, $R_3$, $R_4$, $R_5$ and X have the previously assigned meanings and $A^-$ represents an anion derived from an organic or inorganic acid such as halide, sulphate, phosphate, acetate, propionate etc.

This reduction takes place with the aid of an alkali metal, preferably sodium, in a suitable solvent, preferably an alcohol such as methanol, ethanol or isopropanol.

The compounds of general formula IV or IVA required as starting materials are prepared in a way usual for analogous compounds. An example of the preparation of this compound is shown in the flow sheet hereinbelow.

The compounds according to the invention may occur in 2 diastereo-isomeric forms, namely as cis-compound or as trans-compound. In the cis-compound, the hydrogen atoms present in the bridge between the B and the D ring of the compound of formula I, are in the cis- position with respect to each other. In the trans-compound, the two hydrogen atoms are on opposite sides of the bond.

Both the cis-compounds and the trans-compounds, as well as a mixture of both diastereo-isomers, are included amongst the compounds according to the invention.

The separate cis- and trans-isomers may be prepared from the mixture by means of physico-chemical methods of separation such as fractional crystallization, column chromatography, preparative scale thin layer chromatography or counter-current distribution.

The separate cis- and trans-isomers may, however, also be prepared directly by means of the chemical methods noted above, if the separation has already been performed in an earlier stage of the synthesis and thus use can be made of a separate cis- or trans-starting material.

The separate cis- or trans-isomers of general formula I are generally obtained as a racemate. This racemate may however, if desired, be resolved into the separate optical antipodes with the aid of an optically active acid. Both of the separate optical antipodes are also included amongst the compounds according to the invention. It is however also possible to prepare the optically active compounds in certain cases directly, by making use of an optically active starting material. For example, the compound II with a saturated D-ring is eminently suitble for this direct synthesis.

The separate cis- form of a compound I, in which m=1 and where both benzene rings are substituted in the same way (plane of symmetry:mirror image) provides the optically inactive meso-form, in which case no separate optically active antipodes are possible.

In the compounds according to the invention, an alkyl group with 1–6 carbon atoms is understood to mean both straight-chain and branched-chain alkyl groups such as methyl, ethyl, propyl, isopropyl, butyl, isobutyl, sec.butyl, tert.butyl, pentyl, isopentyl, neopentyl or hexyl.

By an aralkyl group is preferably meant a phenylalkyl group with 7–10 carbon atoms, such as benzyl, phenylethyl, phenylpropyl or 1-methylphenylethyl.

By salts of the compounds according to the general formula I are understood the acid addition salts and quaternary ammonium salts.

The acid addition salts according to the invention are prepared in the appropriate way by allowing the free base I to react with a pharmaceutically acceptable acid. The usual acids in this connection are: hydrochloric acid, hydrogen bromide or iodide, phosphoric acid, acetic acid, propionic acid, glycollic acid, maleic acid, malonic acid, succinic acid, tartaric acid, citric acid, ascorbic acid, salicylic acid or benzoic acid.

The quaternary ammonium salts, and in particular the lower (1–4 C) alkyl quaternary ammonium compounds are obtained by allowing the compounds according to general formula I to react with an alkyl halide, preferably methyl iodide, methyl bromide or methyl chloride.

The nitrogen oxides of the compounds according to general formula I are obtained by oxidation of the free base I with the aid of hydrogen peroxide or a peracid.

It is of course possible to introduce or change the substituents in one or both phenyl rings after the condensation reactions described above. For example, a hydroxyl group present may be converted into an alkoxy group, a methoxy group may be converted into a hydroxy group.

The unsubstituted amine according to the general formula I ($R_5$=H) may be alkylated in the usual way, for example by reaction with an alkyl or aralkyl halide. For this purpose, it is however more usual to acylate the nitrogen atom concerned, with, for example, an acid chloride or anhydride, and subsequently reduce the keto group of the N-acyl derivative obtained. For the introduction of a methyl group at the nitrogen atom, use is preferably made of the Eschweiler-Clarke procedure (using a mixture of formaldehyde and formic acid) or of the reaction with formaldehyde and sodium cyanoborohydride in a suitable solvent, such as acetonitrile.

It is also possible to convert the substituted amine according to formula I ($R_5 \neq H$) into the corresponding unsubstituted amine ($R_5 = H$). A much used method for this purpose consists of the reaction of the alkyl- or aralkyl-substituted amine I with an ester of chloroformic acid or with BrCN, followed by hydrolysis of the product thus obtained.

The compounds according to the invention may be administered by the oral, rectal and parenteral routes, preferably in a daily dosage of 0.01-10 mg per kg body weight.

When mixed with suitable excipients, the compounds may be processed to give solid dosage forms such as pills, tablets, suppositories or dragees. Optionally mixed with excipients, they may be made into capsules. With the aid of suitable liquids, the compounds may also be used as injection preparations in the form of solutions, emulsions or suspensions.

The compounds according to general formula I, which are preferably used, are those compounds in which X represents oxygen or a —$CH_2$— group.

Preference is furthermore accorded to compounds of general formula I, in which the benzene rings are not substituted at all ($R_1$, $R_2$, $R_3$ and $R_4$ are each hydrogen) or in which one or both benzene-rings is (are) substituted by one or two substituents.

Amongst those preferred substituted compounds of formula I, the compounds having one or two substituents (at one or both benzene rings) consisting of methyl, halogen or methoxy, particularly in the positions 6 and/or 12 when the D-ring is a 6-membered ring and in the positions 5 and/or 11 when the D-ring is a 5-membered ring are further preferred.

From pharmacological point of view most interesting compounds I are found in the cis- and trans-isomers when the D-ring is 5-membered (m=1) and in the trans-isomers when the D-ring is 6-membered (m=2).

Preferred compounds in this respect are the cis- and trans-isomers of the compounds of formula I, in which X is methylene or oxygen, m has the value 1, $R_5$ is methyl and the benzene rings are unsubstituted or provided with a methyl substituent preferably at the positions 5 and/or 11, and the trans-isomers of corresponding compounds I, in which m has the value 2.

Preferably each of $R_1$ through $R_4$ is hydrogen, a halogen, methyl, or methoxy. It is also preferred that all of $R_1$ through $R_5$ are hydrogen, or that no more than one or two of $R_1$ through $R_4$ are methyl. $R_1$ may preferably also be trifluromethyl; $R_5$ preferably may be methyl or propyl.

The following nomenclature and numbering has been used in the Examples.

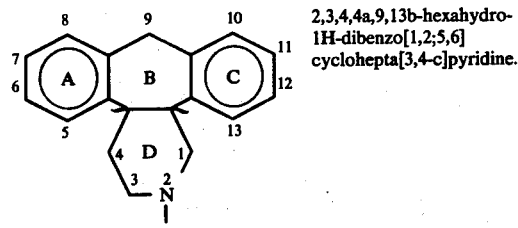

2,3,4,4a,9,13b-hexahydro-1H-dibenzo[1,2;5,6]cyclohepta[3,4-c]pyridine.

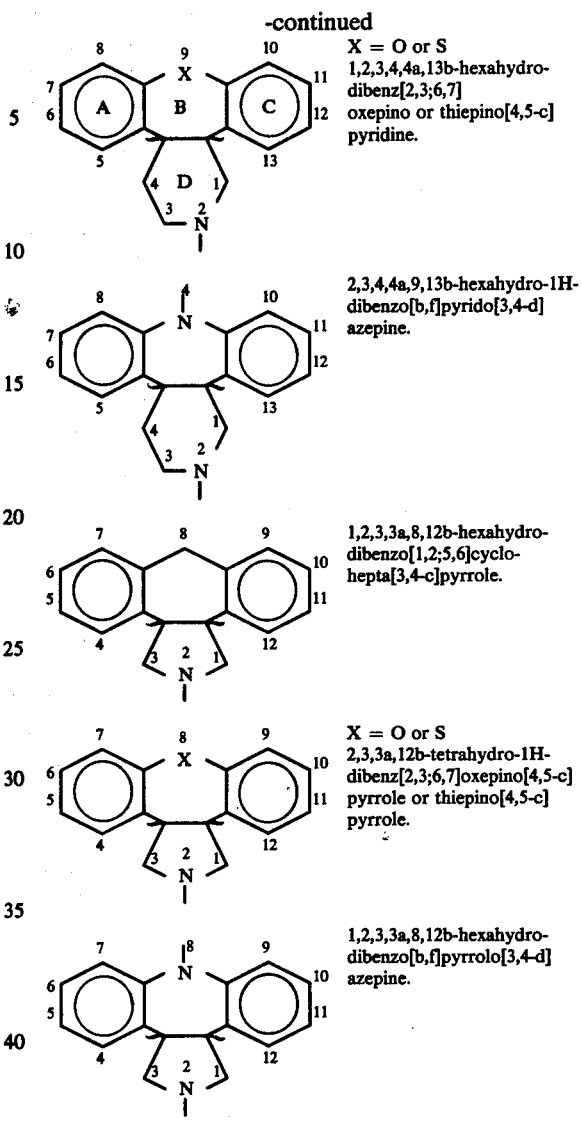

1,2,3,4,4a,13b-hexahydrodibenz[2,3;6,7]oxepino or thiepino[4,5-c]pyridine. X = O or S 2,3,4,4a,9,13b-hexahydro-1H-dibenzo[b,f]pyrido[3,4-d]azepine.

1,2,3,3a,8,12b-hexahydrodibenzo[1,2;5,6]cyclohepta[3,4-c]pyrrole.

2,3,3a,12b-tetrahydro-1H-dibenz[2,3;6,7]oxepino[4,5-c] pyrrole or thiepino[4,5-c]pyrrole. X = O or S 1,2,3,3a,8,12b-hexahydrodibenzo[b,f]pyrrolo[3,4-d]azepine.

EXAMPLE I 2-methyl-1,2,3,4,4a,13b-hexahydrodibenz[2,3;6,7]oxepino [4,5-c]pyridine maleate.

A. A solution of 35 g 2-methyl-3,4-dihydrodibenz [2,3;6,7]oxepino[4,5-c]pyridin-1(2H)-one (melting point 172°-174° C.) in 2500 ml dry methanol is heated to the boiling point, after which 140 g magnesium is added to the solution in 2 portions of each 70 g. The mixture is subsequently refluxed for about 1 hour, after which it is cooled and evaporated to dryness. 1100 mL 6N hydrochloride acid is then added to the residue slowly with cooling and the mixture is stirred for a while. The resultant precipitate is filtered off and taken up in methylene chloride. The solution is washed with water until it gives a neutral reaction, dried over sodium sulphate, and evaporated to dryness. Yield 36.2 g of a mixture of cis- and trans-2-methyl-3,4,4a,13b- tetrahydrodibenz[2,3;6,7]oxepino[4,5-c]pyridin-1(2H)-one, which is subsequently separated and purified by means of $SiO_2$ column chromatography with ethyl acetate as eluent.

Yield: 3.6 g trans-compound, melting point 149°–151° C., R_f in ethyl acetate=0.43 (SiO_2) and 22.4 g cis-compound, melting point 155°–157° C., R_f in ethyl acetate=0.31 (SiO_2).

B. A solution of 3.6 g of the trans-compound obtained in A. in 160 ml dry ether is added slowly over a period of about 10 minutes to a stirred suspension of 4 g LiAlH_4 in 400 mL dry ether.

The reaction mixture is subsequently stirred for a further 30 minutes at room temperature and then cooled to about 0° C. After the addition of 16 ml water, the mixture is filtered and the filtrate is evaporated to dryness under vacuum. The residue is then dissolved in 45 ml ethanol and 1.6 g maleic acid is added to the solution. The maleic acid dissolves after warming for a while. After cooling and the addition of ether, a precipitate is obtained which is separated by filtration and further purified by means of crystallization or column chromatography.

Yield: 3.9 g trans-2-methyl-1,2,3,4,4a,13b-hexahydrodibenz[2,3;6,7]oxepino[4,5-c]pyridine maleate; melting point 175° C.

R_F in methanol:acetone (9:1=0.40 (SIO_2).

The corresponding cis-compound is obtained in an analogous fashion by starting from the cis-compound obtained in A. Melting point of the maleate salt: 189°–192° C.

Treatment of the free trans-base with methyl iodide gives the corresponding iodo-methylate.

EXAMPLE II

The compounds listed below are prepared in a way corresponding to that described in Example I: cis-2-methyl-2,3,4,4a,9,13b-hexahydro-1H-dibenzo[1,2;5,6]-cyclohepta[3,4-c]pyridine maleate, m.p. 209° C.; trans-2-methyl-2,3,4,4a,9,13b-hexahydro-1H-dibenzo [1,2;5,6]cyclohepta[3,4-c]pyridine maleate, m.p. 177° C.; cis-2,3,4a,9,13b-hexahydro-1H-dibenzo[1,2;5,6]cyclohepta [3,4-c]pyridine, oil, R_f in methylenechloride:-methanol (7:3)=0.14 on SIO_2; trans-2,3,4,4a,9,13b-hexahydro-1H-dibenzo[1,2;5,6]cyclohepta[3,4-c]pyridine maleate, m.p. 171°–173° c.; cis and trans mixture of 2-methyl-12-methoxy-2,3,4,4a,9,13b-hexahydro-1H-dibenzo[1,2;5,6]cyclohepta[3,4-c]pyridine, (oil); cis-2,6-dimethyl-2,3,4,4a,9,13b-hexahydro-1H-dibenzo-[1,2;5,6]cyclohepta[3,4-c]pyridine, m.p. 142°–145° C. trans-2,6-dimethyl-2,3,4,4a,9,13b-hexahydro-1H-dibenzo-[1,2;5,6]cyclohepta[3,4-c]pyridine-maleate, m.p. 182° C.; cis and trans mixture of 2-methyl-10,11-dimethoxy-1,2,3,4,4a,13b-hexahydrodibenz[2,3;6,7]oxepino[4,5-c]pyridine (oil); cis and trans mixture of 2,12 -dimethyl-1,2,3,4,4a,13b-hexahydrodibenzo[2,316,719 oxepino[4,5-c](oil); cis-2,6-dimethyl-1,2,3,4,4a,13b-hexahydrodibenzo[2,3;6,7]-oxepino[4,5-c]pyridine maleate, m.p. 177°–179° C.; trans-2,6-dimethyl-1,2,3,4,4a,13b-hexahydro-dibenz-[2,3;6,7]oxepino[4,5-c]pyridine maleate, m.p. 180° C.; cis-2,12-dimethyl-1,2,3,4,4a13b-hexahydro-dibenz-[2,3;6,7]oxepino[4,5-c]pyridine maleate, m.p. 181°–183° C.; trans-2,12-dimethyl-1,2,3,4,4a,13b-hexahydro-dibenz-[2,3;6,7]oxepino[4,5-c]pyridine maleate, m.p. 146°–149° C.; cis-2-methyl-12-chloro-1,2,3,4,4a,13b-hexahydro-dibenz-[2,3;6,7]oxepino[4,5-c]pyridine maleate, m.p. 185° C.; trans-2-methyl-12-chloro-1,2,3,4,4a,13b-hexahydro-dibenz- [2,3;6,7]oxepino[4,5-c]pyridine (oil), R_f in methylene-chloride:methanol (9:1)=0.65 on SIO_2; mixture of cis and trans 2-methyl-6-trifluoromethyl-1,2,3,4,4a,13b-hexahydrodibenz[2,3;6,7]oxepino[4,5-c]pyridine (oil); cis-2-methyl-1,2,3,4,4a,13b-hexahydro-dibenzo[2,3;6,7]-thiepino[4,5-c]pyridine (oil), R_f in methanol-acetone (9:1)=0.45 on SIO_2; trans-2-methyl-1,2,3,4,4a,13b-hexahydro-dibenzo[2,3;6,7]-thiepino[4,5-c]pyridine maleate, m.p. 181°–183° C.; cis-2,9-dimethyl-2,3,4,4a,9,13b-hexahydro-1H-dibenzo[b,f]-pyrido[3,4-d]azepine (oil); trans-2,9-dimethyl-2,3,4,4a,9,13b-hexahydro-1H-dibenzo- ]b,f]pyrido[3,4-d]-azepine (oil); mixture of cis and trans 2-methyl-12-t.butyl-1,2,3,4,4a,13b- hexahydrodibenz[2,3;6,7]oxepino[4,5-c]pyridine (oil); mixture of cis and trans 2-propyl-1,2,3,4,4a,13b-hexahydrodibenz[2,3;6,7]oxepino[4,5-c]pyridine (oil); cis-2,12-dimethyl-1,2,3,4,4a,13b-hexahydro-dibenzo[2,3;6,7]-thiepino[4,5-c]pyridine maleate, m.p. 150° C. and the corresponding trans-isomer (malaeate) m.p. 170° C.; cis-2-methyl-12-isopropyl-1,2,3,4,4a,13b-hexahydrodibenz[2,3;6,7]oxepino[4,5-c]pyridine maleate, m.p. 136° C. and the corresponding trans-isomer (maleate), m.p. 183° C.

EXAMPLE III cis-2-methyl-1,2,3,3a,8,12b-hexahydro-dibenzo[1,2;5,6-cyclohepta[3,4-c]pyrrole.

0.7 g cis-2-methyl-3,3a,8,12b-tetrahydro-dibenzo[1,2;5,6]cyclohepta[3,4-c]pyrrol-1(2H)-one is dissolved in 25 ml dry ether/tetrahydrofuran (1:1). This solution is slowly added at 0° C. to a suspension of 0.35 g LiAlH_4 in 20 ml ether/t.h.f. (1:1). After stirring for 15 minutes, water is added and the mixture is then filtered. The filtrate is subsequently evaporated to dryness under vacuum. This gives an oily residue, weighing about 0.7 g. Addition of 8 ml ethanol to this residue results in the formation of a precipitate, which is filtered off. [The crystalline product thus obtained is recrystallized, giving 0.25 g 2-methyl-2,3,3a,8-tetrahydro-dibenzo[1,2;5,6-]cyclohepta[3,4-c]pyrrole of melting point 128°–131° C. (= enamine according to formula III)].

The filtrate is subsequently evaporated to dryness and the residue is chromatographed on a silica gel column with methanol/acetone (9:1) as eluent. Yield 0.3 g of the product named in the title. Melting point 97°–98° C.; R_f in toluene:ethanol (8:2) =0.43 on SiO_2.

Treatment of this latter compound with methyl iodide gives the corresponding iodo-methylate; melting point 287°–291° C.

EXAMPLE IV

The compounds listed below are prepared in a way corresponding to that described in Example III; in each case, in addition to the compounds named, the corresponding enamine (according to formula III) is also isolated from the reaction mixture. trans-2-methyl-1,2,3,3a,8,12b-hexahydro-dibenzo[1,2:5,6]cyclohepta[3,4-c]pyrrole, m.p. 82°–84° C.; mixture of cis and trans 2-methyl-5-methoxy-1,2,3,3a,8,12b-hexahydro-dibenzo[1,2;5,6]cyclohepta[3,4-c]pyrrole (oil); cis-2-methyl-2,3,3a,12b-tetrahydro-1H-dibenz[2,3;6,7]-oxepino[4,5-c]pyrrole maleate, m.p. 142°–144° C. and the corresponding chloromethylate, m.p. 297°–308° C.; trans-2-methyl-2,3,3a,12b-tetrahydro-1H-dibenz[2,3;6,-7]oxepino[4,5-c]pyrrole fumarate, m.p. 199°–200° C. and the corresponding maleate, m.p. 189° C.;

mixture of cis and trans 2-methyl-6,7-dimethoxy-2,3,3a,12b-tetrahydro-1H-dibenz[2,3;6,7]oxepino[4,5-c]pyrrole, (oil);

cis-2-methyl-5-chloro-2,3,3a,12b-tetrahydro-1H-dibenz[2,3;6,7]oxepino[4,5-c]pyrrole maleate, m.p. 168° Cl;
trans-2-methyl-5-chloro-2,3,3a,12b-tetrahydro-1H-dibenz[2,3;6,7]oxepino[4,5-c]pyrrole maleate, m.p. 141° C.;
cis-2,5-dimethyl-2,3,3a,12b-tetrahydro-1H-dibenz[2,3;6,7]oxepino[4,5-c]pyrrole, m.p. 99°–101° C.;
trans-2,5-dimethyl-2,3,3a,12b-tetrahydro-1H-dibenz[2,3;6,7]oxepino[4,5-c]pyrrole, m.p. 61°–62° C.;
mixture of cis and trans 2-methyl-5-chloro-1,2,3,3a,8,12b-hexahydro-dibenzo[1,2;5,6]cyclohepta[3,4-c]pyrrole, (oil);
mixture of cis and trans 2-methyl-2,3,3a,12b-tetrahydro-1H-dibenzo[2,3;6,7]thiepino[4,5-c]pyrrole, (oil).

EXAMPLE V 2-methyl-1,2,3,3a,8,12b-hexahydro-dibenzo[1,2;5,6]cyclohepta[3,4-c]pyrrole.

250 mg 2-methyl-2,3,3a,8-tetrahydro-dibenzo[1,2:6,7]-cyclohepta[3,4-c]pyrrole, obtained in Example III as a by-product of the reduction with LiAlH$_4$, is dissolved in 35 ml ethanol, after which 750 mg sodium borohydride is added to the solution and the whole is stirred for 2 hours at room temperature. 2N CH$_3$COOH is subsequently added to the reaction mixture, which is then diluted with water and extracted with methylene chloride. The extracts obtained are evaporated to dryness and the residue is purified by chromatography on a silica gel column with methanol/acetone (9:1) as eluent.

Yield: 165 mg cis-2-methyl-1,2,3,3a,8,12b-hexahydro-dibenzo[1,2;5,6]-cyclohepta[3,4-c]pyrrole, melting point 97°–98° C., and 25 mg trans-2-methyl-1,2,3,3a,8,12b-hexahydro-dibenzo[1,2;5,6]cyclohepta[3,4-c]pyrrole, melting point 82°–84° C.

The following compounds are prepared in a corresponding fashion:
cis-2-methyl-2,3,3a,12b-tetrahydro-1H-dibenz[2,3;6,7]oxepino[4,5-c]pyrrole maleate, m.p. 143°–144° C.;
cis-2,5-dimethyl-2,3,3a,12b-tetrahydro-;b 1H-dibenz[2,3;6,7]oxepino[4,5-c]pyrrole, m.p. 99°–101° C.;
cis-2-methyl-5-chloro-2,3,3a,12b-tetrahydro-1H-dibenz[2,3;6,7]oxepino[4,5-c]pyrrole maleate, m.p. 166°–169° C.;
cis-2-methyl-1,2,3,4,4a,13b-hexahydro-dibenz[2,3;6,7]oxepino[4,5-c]pyridine maleate, m.p. 174°–175° C.;
cis-2-methyl-2,3,4,4a,9,13b-hexahydro-1H-dibenzo[1,2:5,6]cyclohepta[3,4-c]pyridine maleate, m.p. 207°–209° C. and the corresponding trans isomer (maleate salt), m.p. 175°–176° C.

EXAMPLE VI

Trans-2-methyl-2,3,4,4a,9,13b-hexahydro-1H-dibenz[1,2;5,6]cyclohepta[3,4-c]pyridine maleate.

A mixture of 50 mg trans-2,3,4,4a,9,13b-hexahydro-1H-dibenzo[1,2;5,6]cyclohepta[3,4-c]pyridine, 1 ml formic acid and 1 ml 35% formaldehyde solution is heated on a steambath for 3 hours. The reaction mixture is then made alkaline and extracted with ether. The organic phase is washed with H$_2$O dried over Na$_2$SO$_4$ and evaporated to dryness, after which the residue is treated with maleic acid.

Yield: 48 mg; melting point 175°–176° C.

EXAMPLE VII 2-methyl-2,3,4,4a,9,13b-hexahydro-1H-dibenzo[1,2;5,6]cyclohepta[3,4-c]pyridine.

4 g Sodium is added with stirring and under a nitrogen atmosphere to a suspension of 0.5 g 2-methyl-9H-dibenzo[1,2;5,6]cyclohepta[3,4-c]pyridinum iodide (formula IV, melting point > 300° C.) in 50 ml ethanol, after which the mixture is refluxed for 1 hour. The reaction mixture is then poured out into H$_2$O and extracted with methylene chloride. The organic phase is washed with H$_2$O, dried over Na$_2$SO$_4$ and evaporated to dryness.

Yield: 260 mg (76%) of a mixture of cis- and trans-2-methyl-2,3,4,4a,9,13b-hexahydro-1H-dibenzo[1,2;5,6]-cyclohepta[3,4-c]pyridine.

R$_f$ in toluene:ethanol (7:3)=0.27 for the trans-compound and 0.65 for the cis-compound.

The isolation of the individual stereo-isomers is achieved by means of column chromatography followed by conversion to the maleate.

Melting point of the trans-compound as maleate: 177° C.

Melting point of the cis-compound as maleate: 208°–209° C.

EXAMPLE VIII

The following compounds are prepared in a way corresponding to that described in Example VII:
cis and trans mixture of 2-methyl-12-methoxy-2,3,4,4a,9,13b-hexahydro-1H-dibenzo[1,2;5,6]cyclohepta[3,4-c]pyridine;
cis and trans mixture of 2-methyl-6-chloro-2,3,4,4a,9,13b-hexahydro-1H-dibenzo[1,2;5,6]cyclohepta[3,4-c]pyridine;
cis-2,6-dimethyl-1,2,3,4,4a,13b-hexahydro-dibenz[2,3;6,7]oxepino[4,5-c]pyridine maleate;
trans-2,6-dimethyl-1,2,3,4,4a,13b-hexahydro-dibenz[2,3;6,7]oxepino[4,5-c]pyridine maleate;
cis-2,12-dimethyl-1,2,3,4,4a,13b-hexahydro-dibenz[2,3;6,7]oxepino[4,5-c]pyridine maleate;
trans-2,12-dimethyl-1,2,3,4,4a,113b-hexahydro-dibenz[2,3;6,7]oxepino[4,5-c]pyridine maleate;
mixture of cis and trans 2-methyl-12-chloro-1,2,3,4,4a,13b-hexahydro-dibenz[2,3;6,7]oxepino[4,5-c]pyridine;
cis-2-methyl-1,2,3,4,4a,13b-hexahydro-dibenzo[2,3;6,7]-thiepino[4,5-c]pyridine;
trans-2-methyl-1,2,3,4,4a,13b-hexahydro-dibenzo[2,3;6,7]thiepino[4,5-c]pyridine maleate.

EXAMPLE IX

A. 9H-dibenzo[1,2;5,6]cyclohepta[3,4-c]pyridine

A mixture of 19.9 g 2-methyl-9H-dibenzo[1,2;5,6]cyclohepta[3,4-c]pyridinium iodide (formula IV) and 100 ml ethanolamine is heated with stirring in an oil bath at 160° C. for 2 hours. The reaction mixture is then poured out into H$_2$O and extracted with ether. The organic phase is extracted with dilute HCL, after which the acid aqueous layer is made alkaline and extracted with ether. The ether layer is washed with H$_2$O until neutral, dried over Na$_2$SO$_4$ and evaporated to dryness.

Yield: 7.74 g 9H-dibenzo[1,2;5,6]cyclohepta[3,4-c]pyridine (formula IVA). The residue is crystallized from ethyl acetate/petroleum ether (1:2).

Melting point: 115°–117° C.

Melting point of the HCl salt, obtained by treatment of the free base with HCl: 264°-270° C.

B. 2,3,4,4a,9,13b-hexahydro-1H-dibenzo[1,2;5,6]cyclohepta[3,4-c]pyridine 27 g Sodium is added in portions with stirring and under nitrogen over a period of about 5 hours to a solution of 4.45 g of the free base (obtained in A) in 300 ml ethanol. The temperature is maintained at 80° to 90° C. during this process. After 5½ hours all sodium has dissolved. 250 ml $H_2O$ is then added, after which the ethanol is distilled off under vacuum. The residue is extracted with ether and the organic phase is washed with water until neutral, dried over $Na_2SO_4$, and evaporated to dryness.

Yield: 4.44 g (97.3%) of a mixture of cis- and trans-isomers of the title compound.

$R_f$ in toluene:ethanol (7:3)=0.09 for the cis-compound 0.15 for the trans-compound, and $R_f$ in methylenechloride:methanol (7:3)=0.14 on $SiO_2$ for the cis-compound and 0.66 for the trans-compound.

EXAMPLE X 2-methyl-1,2,3,4,4a,13b-hexahydro-dibenz[2,3;6,7]oxepino[4,5-c]pyridine 380 mg of 2-methyl-3,4-dihydro-dibenz[2,3;6,7]oxepino[4,5-c]pyridin-1(2H)one are dissolved in 40 ml dry tetrahydrofuran. The solution is refluxed under nitrogen atmosphere while introducing diboran (gaz) through the solution for 30 minutes.

Diboran is obtained from the reaction of 1.8 ml $BF_3$-etherate and 450 mg sodium borohydride, in 5 ml diglyme. Refluxing is continued for 3 hours, after which the solution is cooled down and the excess of diboran is removed with ethanol. The mixture is then reduced to a smaller volume by evaporation. To the residue a mixture of concentrated hydrochloric acid and water (1:1) is added and heated until a solution is obtained. After cooling the aqueous layer is made alkaline and extracted with ether. The ether extracts are washed with water, dried and evaporated. Yield 280 mg of a mixture of cis and trans 2-methyl-1,2,3,4,4a,13b-hexahydro-dibenz[2,3;6,7]oxepino[4,5-c]pyridine in a ratio of about 1 to 1.

$R_f$ cis-compound in methanol:acetone (9:1)=0.30 on $SiO_2$ and $R_f$ of the trans-compound 0.36 in the same system.

The same mixture of cis and trans isomers is obtained starting from 2-methyl-dibenz[2,3;6,7]oxepino[4,5-c]pyridin-1(2H)one.

Flow sheet
Preparation of starting materials II and III

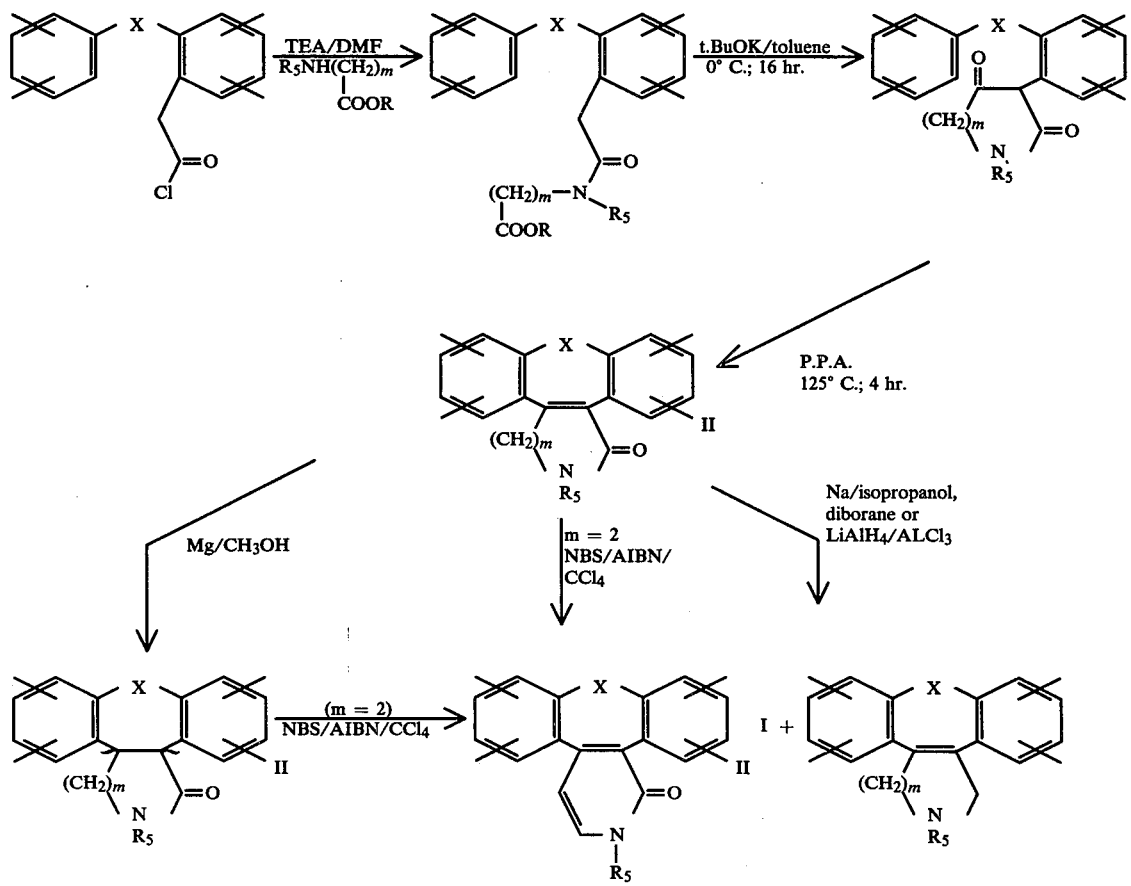

-continued
Flow sheet

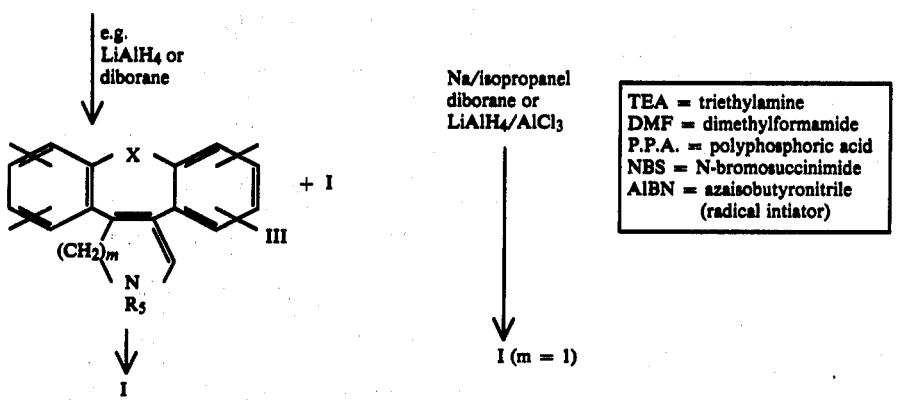

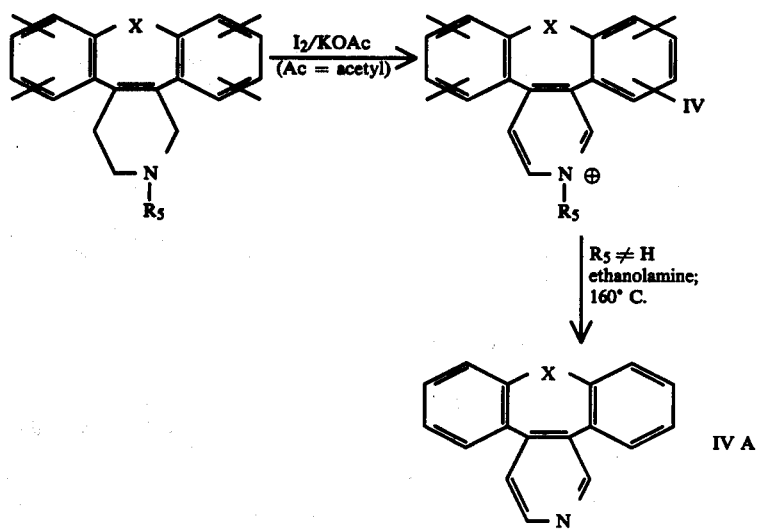

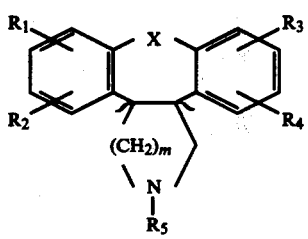

I claim:
1. A compound of the formula

[structure with $R_1$, $R_2$, $R_3$, $R_4$, X, $(CH_2)_m$, N, $R_5$]

or a pharmaceutically acceptable non-toxic salt or nitrogen oxide thereof,
wherein:
$R_1$, $R_2$, $R_3$, and $R_4$ each represent a member selected from the group consisting of hydrogen, hydroxy, halogen, $C_1$-$C_6$ alkyl, $C_1$-$C_6$ alkoxy, $C_1$-$C_6$ alkylthio, and trifluoromethyl;
$R_5$ represents hydrogen, $C_1$-$C_6$ alkyl or aralkyl having from 7 to 10 atoms; atoms
X represents —$CH_2$—; and
m represents the number 2.
2. The compound of claim 1 wherein $R_1$, $R_2$, $R_3$, $R_4$, and $R_5$ are hydrogen.
3. The compound of claim 1 wherein $R_1$ is methyl.

4. The compound of claim 1 wherein $R_1$ and $R_4$ are methyl.
5. The compound of claim 1 wherein $R_1$ is hydrogen.
6. The compound of claim 1 wherein $R_1$ and $R_4$ are halogen.
7. The compound of claim 1 wherein $R_5$ is methyl.
8. The compound of claim 1 wherein $R_3$ is methoxy.
9. The compound of claim 1 wherein $R_1$ is trifluoromethyl.
10. The compound of claim 1 wherein $R_3$ is t.butyl.
11. The compound of claim 1 wherein $R_5$ is propyl.
12. The compound of claim 1 wherein $R_2$ is chlorine.
13. The compound of claim 1 which is cis-2-methyl-2,3,4,4a,9,13b-hexahydro-1H-dibenzo[1,2;5,6]cyclohepta[3,4-c]pyridine maleate.
14. The compound of claim 1 which is trans-2-methyl-2,3,4,4a,9,13b-hexahydro-1H-dibenzo[1,2;4,6]cyclohepta[3,4-c]pyridine maleate.
15. The compound of claim 1 which is cis-2,3,4,4a,9,13b-hexahydro-1H-dibenzo[1,2;5,6]cyclohepta[3,4-c]pyridine.
16. The compound of claim 1 which is trans-2,3,4,4a,9,13b-hexahydro-1H-dibenzo[1,2;5,6]cyclohepta[3,4-c]pyridine maleate.
17. The compound of claim 1 which is 2-methyl-12-methoxy-2,3,4,4a,9,13b-hexahydro-1H-dibenzo[1,2;5,6-]cyclohepta[3,4-c]pyridine.

18. The compound of claim 1 which is cis-2,6-dimethyl-2,3,4,4a,9,13b-hexahydro-1H-dibenzo[1,2;5,6]cyclohepta[3,4-c]pyridine.

19. The compound of claim 1 which is trans-2,6-dimethyl-2,3,4,4a,9,13b-hexahydro-1H-dibenzo[1,2;5,6-]cyclohepta[3,4-c]pyridine-maleate.

20. The compound of claim 1 which is 2-methyl-12-methoxy-2,3,4,4a,9,13b-hexahydro-1H-dibenzo[1,2;5,6-]cyclohepta[3,4-c]pyridine.

21. The compound of claim 1 which is 2-methyl-6-chloro-2,3,4,4a,9,13b-hexahydro-1H-dibenzo[1,2;5,6-]cyclohepta[3,4-c]pyridine.

22. A pharmaceutical composition having sedative, depressive, and neuroleptic properties, comprising:
a pharmaceutically effective amount of a compound of the formula:

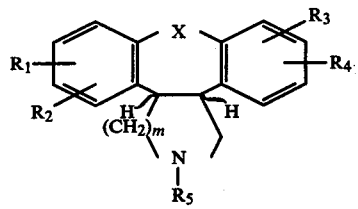

or a pharmaceutically acceptable non-toxic salt or nitrogen oxide thereof;
wherein;
$R_1$, $R_2$, $R_3$, and $R_4$ represent a member selected from the group consisting of hydrogen, hydroxy, halogen, $C_1$–$C_6$ alkyl, $C_1$–$C_6$ alkoxy, $C_1$–$C_6$ alkylthio, and trifluoromethyl;
$R_5$ represents hydrogen, $C_1$–$C_6$ alkyl or aralkyl having from 7 to 10 carbon atoms;
X represents —$CH_2$—; and
m represents the number 2, and a pharmaceutically acceptable carrier.

23. The composition of claim 22 wherein $R_1$, $R_2$, $R_3$, $R_4$ and $R_5$ are hydrogen.

24. The composition of claim 22 wherein $R_1$ is methyl.

25. The composition of claim 22 wherein $R_1$ and $R_4$ are methyl.

26. The composition of claim 22 wherein $R_1$ is halogen.

27. The composition of claim 22 wherein $R_1$ and $R_4$ are halogen.

28. The composition of claim 22 wherein $R_5$ is methyl.

29. The composition of claim 22 wherein $R_5$ is methyl.

30. The composition of claim 22 wherein $R_3$ is methoxy.

31. The composition of claim 22 wherein $R_1$ is trifluoromethyl.

32. The composition of claim 22 wherein $R_3$ is tert-butyl.

33. The composition of claim 22 wherein $R_5$ is propyl.

34. The composition of claim 22 wherein $R_2$ is chlorine.

35. The composition of claim 22 in solid form.

36. Method of reducing tension in humans, comprising administering to a human a tension-reducing amount of a compound of the formula:

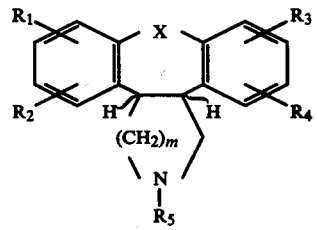

or a pharmaceutically acceptable non-toxic salt or nitrogen oxide thereof;
wherein:
$R_1$, $R_2$, $R_3$, and $R_4$ represent a member selected from the group consisting of hydrogen, hydroxy, halogen, $C_1$–$C_6$ alkyl, $C_1$–$C_6$ alkoxy, $C_1$–$C_6$ alkythio, and trifluoromethyl;
$R_5$ represents hydrogen, $C_1$–$C_6$ alkyl or aralkyl having from 7 to 10 carbon atoms;
X represents —$CH_2$—;
m represents the number 2.

* * * * *

UNITED STATES PATENT OFFICE
CERTIFICATE OF CORRECTION

Patent No. 4,158,059    Dated June 12, 1979

Inventor(s) Willem Jacob VAN DER BURG

It is certified that error appears in the above-identified patent and that said Letters Patent are hereby corrected as shown below:

Change line 2 of the Title from "2,3,4,4A,9,136-HEXAHYDRO-DIBENZ [1,2;5,6-" to --2,3,4,4A,9,13b-HEXAHYDRO-DIBENZ[1,2;5,6- --.

In column 1, line 2, change "2,3,4,4A,9,136-" to --2,3,4,4a,9, 13b- --.

In column 1, lines 17-27, the formula

" 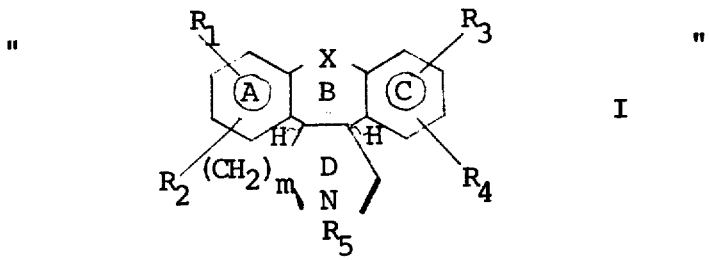 " I should be replaced by

-- 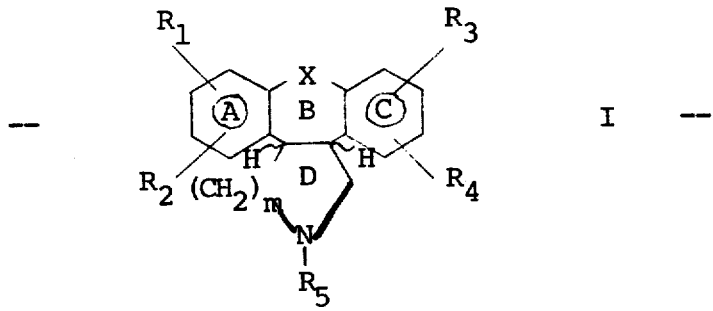 I --

UNITED STATES PATENT OFFICE
CERTIFICATE OF CORRECTION

Patent No. 4,158,059          Dated   June 12, 1979

Inventor(s)  Willem Jacob VAN DER BURG

It is certified that error appears in the above-identified patent and that said Letters Patent are hereby corrected as shown below:

In column 1, line 37, "x" should be replaced by --X--.

In column 2, lines 8-17, replace the formula

"  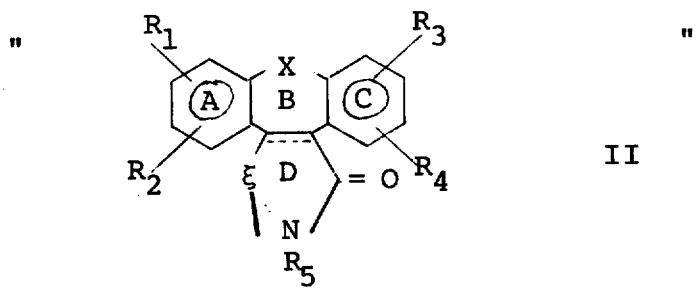  "    II with the formula

--  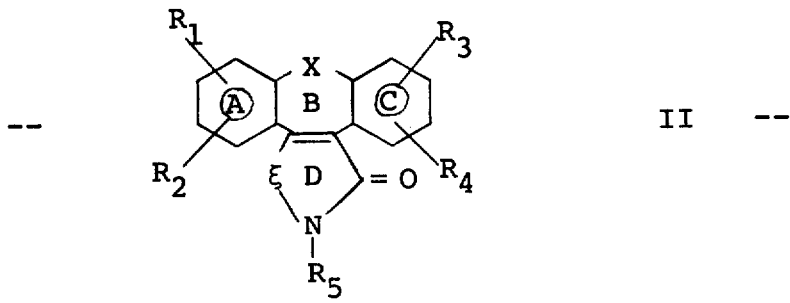    II  --

In column 2, line 50, "hereinbelow" should be replaced by --shown in columns 11-14 herein--.

UNITED STATES PATENT OFFICE
CERTIFICATE OF CORRECTION

Patent No. 4,158,059    Dated  June 12, 1979

Inventor(s)  Willem Jacob VAN DER BURG

It is certified that error appears in the above-identified patent and that said Letters Patent are hereby corrected as shown below:

In column 2, lines 55-63, replace the formula

" 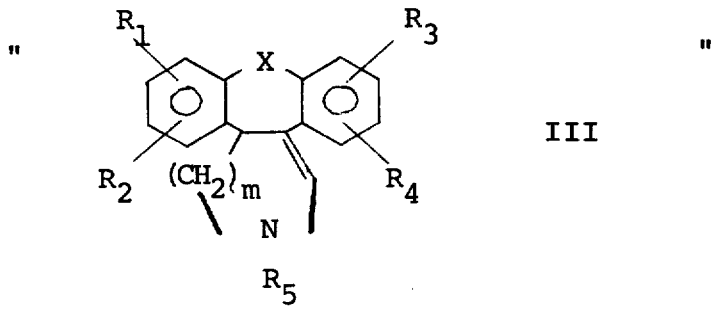  III "

with the formula

-- 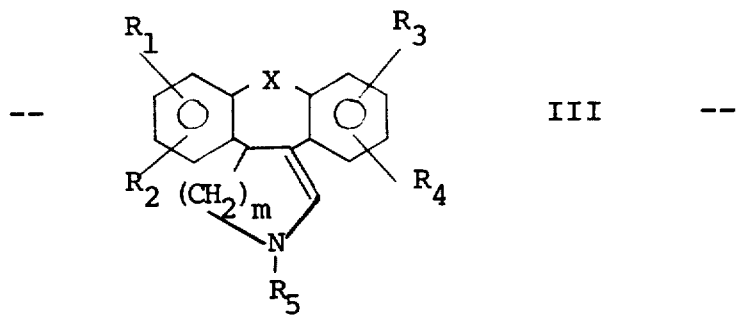  III --

In column 9, line 43, replace the fraction of the formula "-;b 1H-" with -- — -- so that the line reads "cis-2,5-dimethyl-2,3,3a,12b-tetrahydro-1H-".

UNITED STATES PATENT OFFICE
CERTIFICATE OF CORRECTION

Patent No. 4,158,059        Dated June 12, 1979

Inventor(s) Willem Jacob VAN DER BURG

It is certified that error appears in the above-identified patent and that said Letters Patent are hereby corrected as shown below:

In the flow sheet, column 12, the [third] formula

"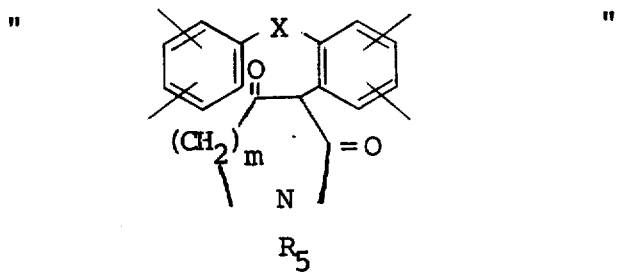"

should be replaced by

--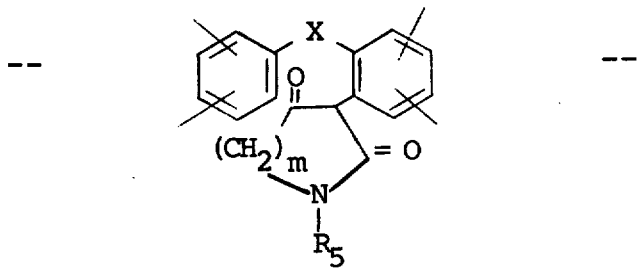--

UNITED STATES PATENT OFFICE
CERTIFICATE OF CORRECTION

Patent No. 4,158,059     Dated  June 12, 1979

Inventor(s)   Willem Jacob VAN DER BURG

It is certified that error appears in the above-identified patent and that said Letters Patent are hereby corrected as shown below:

In the flow sheet, columns 11-12, the [fourth] formula

"  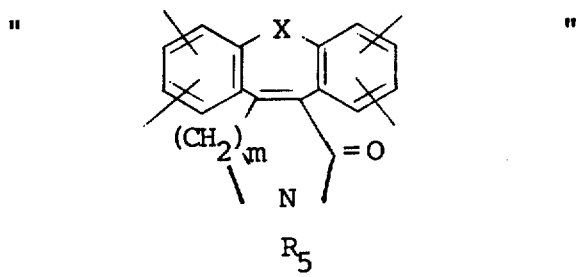  "

should be replaced by the formula

--  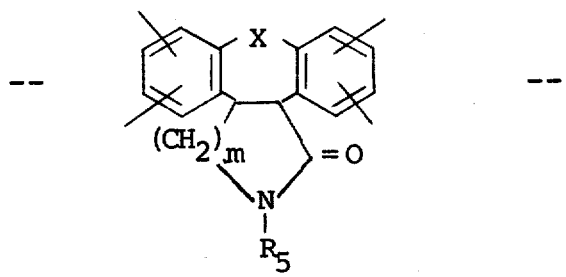  --

UNITED STATES PATENT OFFICE
CERTIFICATE OF CORRECTION

Patent No. 4,158,059          Dated  June 12, 1979

Inventor(s)  Willem Jacob VAN DER BURG

It is certified that error appears in the above-identified patent and that said Letters Patent are hereby corrected as shown below:

In the flow sheet, column 12, [last] formula

" 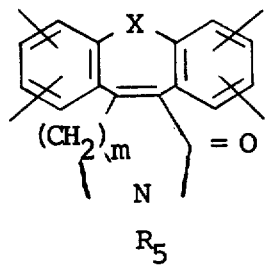 "

should be replaced by the formula

-- 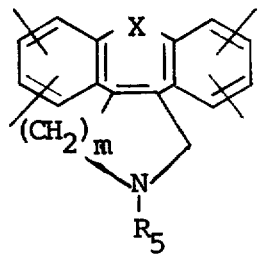 --

UNITED STATES PATENT AND TRADEMARK OFFICE
CERTIFICATE OF CORRECTION

PATENT NO. : 4,158,059
DATED : June 12, 1979
INVENTOR(S) : Willem Jacob VAN DER BURG It is certified that error appears in the above—identified patent and that said Letters Patent is hereby corrected as shown below:

In the flow sheet in column 13, [first] formula

" 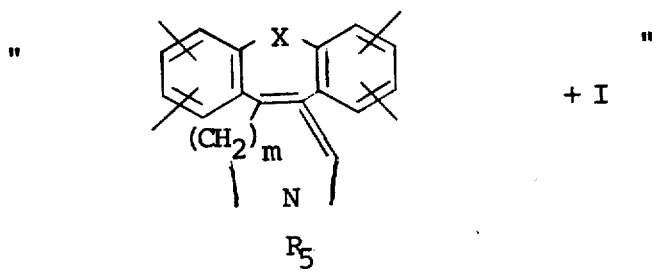 " + I

UNITED STATES PATENT AND TRADEMARK OFFICE
CERTIFICATE OF CORRECTION

PATENT NO. : 4,158,059
DATED : June 12, 1979
INVENTOR(S) : Willem Jacob VAN DER BURG It is certified that error appears in the above—identified patent and that said Letters Patent is hereby corrected as shown below:

should be replaced by the formula

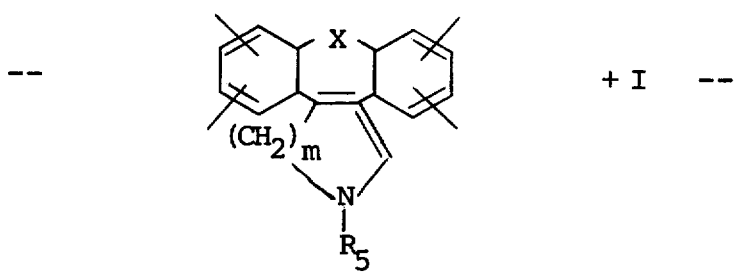

Signed and Sealed this

Eighth Day of January 1980

[SEAL]

Attest:

Attesting Officer

SIDNEY A. DIAMOND
Commissioner of Patents and Trademarks